United States Patent
Kawamata et al.

(10) Patent No.: US 6,293,151 B1
(45) Date of Patent: Sep. 25, 2001

(54) BALL BEARING INSPECTION APPARATUS

(75) Inventors: Takeo Kawamata; Takashi Maeda; Hiroshi Shibazaki, all of Kanagawa (JP)

(73) Assignee: NSK Ltd., Tokyo (JP)

( * ) Notice: Subject to any disclaimer, the term of this patent is extended or adjusted under 35 U.S.C. 154(b) by 0 days.

(21) Appl. No.: 09/497,516

(22) Filed: Feb. 4, 2000

(30) Foreign Application Priority Data

Feb. 4, 1999 (JP) .................................................. 11-027623
Jan. 17, 2000 (JP) .................................................. 12-008032

(51) Int. Cl.⁷ .................................................. G01M 19/00
(52) U.S. Cl. ................................................. 73/593; 73/865.8
(58) Field of Search ........................ 73/660, 788, 862.49, 73/593, 865.8, 666

(56) References Cited

U.S. PATENT DOCUMENTS

| | | | |
|---|---|---|---|
| 4,551,677 | * 11/1985 | Bankston | 73/37.5 |
| 4,729,239 | * 3/1988 | Gordon | 73/593 |
| 5,012,116 | * 4/1991 | Russell | 250/571 |
| 5,210,591 | * 5/1993 | DeGroot | 356/357 |
| 5,889,218 | * 3/1999 | Sato et al. | 73/865.8 |

FOREIGN PATENT DOCUMENTS

| | | | |
|---|---|---|---|
| 7-167790 | 7/1995 | (JP) | G01N/21/88 |
| 10-197403 | 7/1998 | (JP) | G01M/13/04 |
| 10-307081 | 11/1998 | (JP) | G01M/13/04 |

OTHER PUBLICATIONS

Patent Abstracts of Japan 10307081 A Nov. 11, 1998.
Patent Abstracts of Japan 10197403 A Jul. 31, 1998.
Patent Abstracts of Japan 07167790 A Jul. 4, 1995.

* cited by examiner

Primary Examiner—Hezron Williams
Assistant Examiner—Jacques Saint-Surin
(74) Attorney, Agent, or Firm—Sughrue, Mion, Zinn, Macpeak & Seas, PLLC

(57) ABSTRACT

A ball bearing inspection apparatus 1 comprising: a rotation shaft 3 fitted to one (for example, inner race 7) of inner and outer races 7 and 9 for rotating one race while limiting the movement of one race in an axial direction of the rotation shaft 3; a press plate 13 disposed on an opposite side of the rotation shaft 3 with respect to a ball bearing 5 for pressing the other race (for example, outer race 9) in the axial direction of the rotation shaft 3 while limiting the rotation of the other race; and a press-back plate 33 provided so as to be movable in the axial direction of the rotation shaft 3 for pressing back the other race in a direction reverse to the pressing direction of the press plate 13. Hence, the ball bearing inspection apparatus can inspect a large area of ball surfaces in a short time at one installing try.

17 Claims, 9 Drawing Sheets

PRESS BACK BY A VERY SMALL AMOUNT

BALL BEARING INSPECTION APPARATUS

BACKGROUND OF THE INVENTION

1. Field of the Invention

The present invention relates to a ball bearing inspection apparatus for inspecting a ball bearing for surface defects of rolling elements (balls), or the like, interposed between inner and outer races of the ball bearing by detecting vibration generated when rotating the inner and outer races relatively to each other.

2. Description of the Related Art

In a ball bearing incorporated in a precision machine such as a hard disk driving device, or the like, there is a possibility that vibration may be caused by rotation even in the case where a surface of any one of races or balls has a little defect. Therefore, the ball bearing to be incorporated in such a precision machine must be individually inspected for defects of ball surfaces, or the like, by a ball bearing inspection apparatus.

As this type ball bearing inspection apparatus, there is known a conventional apparatus for inspecting a ball bearing for defects by detecting vibration (sound) caused by rotation when relatively rotating inner and outer races of the ball bearing to each other. For example, the conventional ball bearing inspection apparatus is formed so that an outer race is rotated by a rotation shaft in the condition that an inner race is fixed to a stationary shaft. On this occasion, the stationary shaft is pressed with a predetermined load in an axial direction by a cylinder. In this manner, the stationary shaft press the inner race to thereby apply a pre-load to balls. The magnitude of the pre-load is set to be equal to that in use of the ball bearing. In this condition, vibration (sound) caused by rotation is detected by a vibrometer (mircophone), and a judgment is made on the basis of a result of the detection as to whether any one of ball surfaces has a defect or not.

The aforementioned conventional ball bearing inspection apparatus is, however, able to inspect no area but a constant contact area (running trace) of ball surfaces because the balls are loaded with a predetermined constant load (pre-load) in the inspecting operation (even though there is a clearance in the ball bearing itself), so that there is no large change in balls' own rotation axes. There is a possibility that a large part of the ball surfaces except the range of the running trace is unable to be inspected.

On the other hand, changing the load to be applied in the axial direction might be thought of. The balls' own rotation axes are, however, unable to be changed greatly by such a simple means of changing the load. There is still a possibility that a lot of portions which have not been inspected yet might be left.

In addition, applying a pre-loading the balls in a reverse direction to change the balls' own rotation axes by inverting an installing posture of the ball bearing as an object into the ball bearing inspection apparatus might be thought of. Installing operation (that is, an operation in which the ball bearing is installed into the ball bearing inspection apparatus), however, has to be repeated by a plurality of times. There is an expected problem that a long time is required for the inspection.

SUMMARY OF THE INVENTION

The present invention is designed in consideration of the aforementioned circumstances and it is an object thereof to provide a ball bearing inspection apparatus in which a large area of ball surfaces can be inspected in a short time at one installing try.

In order to achieve the above object, according to an aspect of the present invention, there is provided a ball bearing inspection apparatus for inspecting a ball surface state of a ball bearing by measuring vibration generated while relatively rotating inner and outer races of the ball bearing, comprising: a rotation shaft fitted to one of the inner and outer races for rotating the one race while limiting the movement of the one race in an axial direction of the rotation shaft; a press plate disposed on an opposite side of the rotation shaft with respect to the ball bearing for pressing the other race in the axial direction of the rotation shaft while limiting the rotation of the other race; and a press-back plate provided so as be movable in the axial direction of the rotation shaft for pressing back the other race in a direction reverse to the pressing direction of the press plate.

In this ball bearing inspection apparatus, when the rotation shaft is rotated, either one of inner and outer races fitted to the rotation shaft is rotated. Hence, the inner and outer races rotate relatively to each other. When the other one of the inner and outer races is pressed by the press plate in this condition, the inner and outer races are displaced relatively to each other in an axial direction of the rotation shaft. When the other one of the races is contrariwise pressed back by the press-back plate in a direction reverse to the pressing direction of the press plate, the inner and outer races are displaced in an axial direction reverse to the aforementioned direction of the displacement thereof. Hence, the pressing direction applied to the other one of the inner and outer races is changed over to the one or the other one of the axial directions, by which rotation axes of the balls interposed between the inner and outer races change. As a result, contact surfaces of the balls change. Hence, a larger area of the contact surfaces can contribute to the measurement at an installing try or a small number of installing tries, so that the whole area of the contact surfaces of the balls can be measured in a short time.

A ball bearing inspection method using the ball bearing inspection apparatus according to the present invention is a ball bearing inspection method for inspecting a ball surface state of a ball bearing by measuring vibration generated while relatively rotating inner and outer races of the ball bearing. The method comprises the steps of: rotating one of the inner and outer races of the ball bearing by a rotation shaft; pressing the other of the inner and outer races in an axial direction of the rotation shaft while limiting the rotation of the other race by use of a press plate disposed on an opposite side of the rotation shaft with respect to the ball bearing; pressing back the other race in a direction reverse to the pressing direction of the press plate by use of a press-back plate provided movably in the axial direction of the rotation shaft; and pressing the other race in the axial direction of the rotation shaft again by use of the press plate after removing the pressure based on the press-back plate; wherein the pressing step, the pressing-back step and the re-pressing step are repeated successively by a predetermined number of times to thereby inspect the ball surface state of the ball bearing on the basis of vibration measured in the pressing step.

In this ball bearing inspection method, the other one of the relatively rotating inner and outer races is pressed by the press plate and then pressed back in a reverse direction by the press-back plate and then pressed in the axial direction again by the press plate. Hence, whenever the pressing direction is changed over, the rotation axes of the balls interposed between the inner and outer races change and the contact surfaces of the balls change. Hence, when the pressing step, the pressing-back step and the re-pressing step are repeated by a predetermined number of times to thereby inspect the ball surface state of the ball bearing on the basis of vibration measured in the pressing step, new surfaces of ball come into contact successively to make it possible to inspect a wider range of the ball surfaces as the number of changing-over tries increases.

Further, the ball bearing inspection method using the ball bearing inspection apparatus according to the present invention may be of the type for inspecting a ball surface state of a ball bearing by measuring vibration generated in a vibrometer attached to a press plate while relatively rotating inner and outer races of the ball bearing in the condition that a rotation shaft is removably attached to either one of the inner circumference of the inner race or the outer circumference of the outer race in the ball bearing and that a thrust load is applied to an end surface of the other of the inner and outer races by use of the press plate to thereby apply a pre-load to the bearing. In the ball bearing inspection method, a press-back plate may be provided on a side opposite to the press plate with respect to the ball bearing so as to press back the other race in a direction reverse to the pressing direction of the press plate so that thrust loads in opposite axial directions are alternately applied to the other race by use of the press plate and the press-back plate during the rotation of the balls to change the balls' own rotation axes to thereby change the running trace of the balls at the time of the measurement.

In the aforementioned ball bearing inspection method, it is preferable that the rotation axis of each ball of the bearing in the case where a thrust load is imposed on the bearing by the press plate and the rotation axis of the ball in the case where a thrust load is imposed on the bearing by the press-back plate have inclinations opposite to each other with respect to the rotation shaft. Hence, the balls' own rotation axes change largely, so that the whole area of the ball surfaces can be measured quickly.

Further, the number of changing-over (inspection) tries is preferably set to be larger than a value to make the rate of the running area (inspected area) to the ball surface area to be not lower than 80% when the running area is calculated on the basis of the following calculation formula $$X=[1-\{1-(S/100)^N\}]\times 100$$

in which:

S [%] is the rate of the running area (inspected area) to the ball surface area at one changing-over (inspection) try;

N [times] is the number of changing-over (inspection) tries; and

X [%] is the rate of the running area (inspected area) to the ball surface area at N changing-over (inspection) tries.

More preferably, the number of changing-over (inspection) tries may be set to be larger than N in which the rate X of the running area (inspected area) to the ball surface area is not lower than 98%. In this case, there is little missing of defects, so that greater improvement in detecting ability is attained.

Further, the ball bearing inspection apparatus for inspecting a ball surface state of a ball bearing by measuring vibration generated while relatively rotating inner and outer races of the ball bearing, comprises: a rotation shaft fitted to one of the inner and outer races for rotating the one race while limiting the movement of the one race in an axial direction of the rotation shaft; a press plate disposed on an opposite side of the rotation shaft with respect to the ball bearing for pressing the other race in the axial direction of the rotation shaft while limiting the rotation of the other race; and a press-back plate provided so as be movable in the axial direction of the rotation shaft for pressing back the other race in a direction reverse to the pressing direction of the press plate; wherein the ball bearing inspection apparatus performs the inspection in accordance with the aforementioned ball bearing inspection method.

Further, each of the press plate and the press-back plate may be formed so that a thrust load is imposed by drive of a servo-motor. Hence, drive control for pre-loading can be made easily, so that the driving mechanism can be simplified.

In addition, a damper material may be preferably interposed between the press plate and the drive shaft in the ball bearing inspection apparatus so that noise of vibration transmitted from the drive shaft is blocked to improve accuracy in vibration measurement.

DESCRIPTION OF THE PREFERRED EMBODIMENTS

Preferred embodiments of the ball bearing inspection apparatus according to the present invention will be described below in detail with reference to the drawings.

Figure 1:
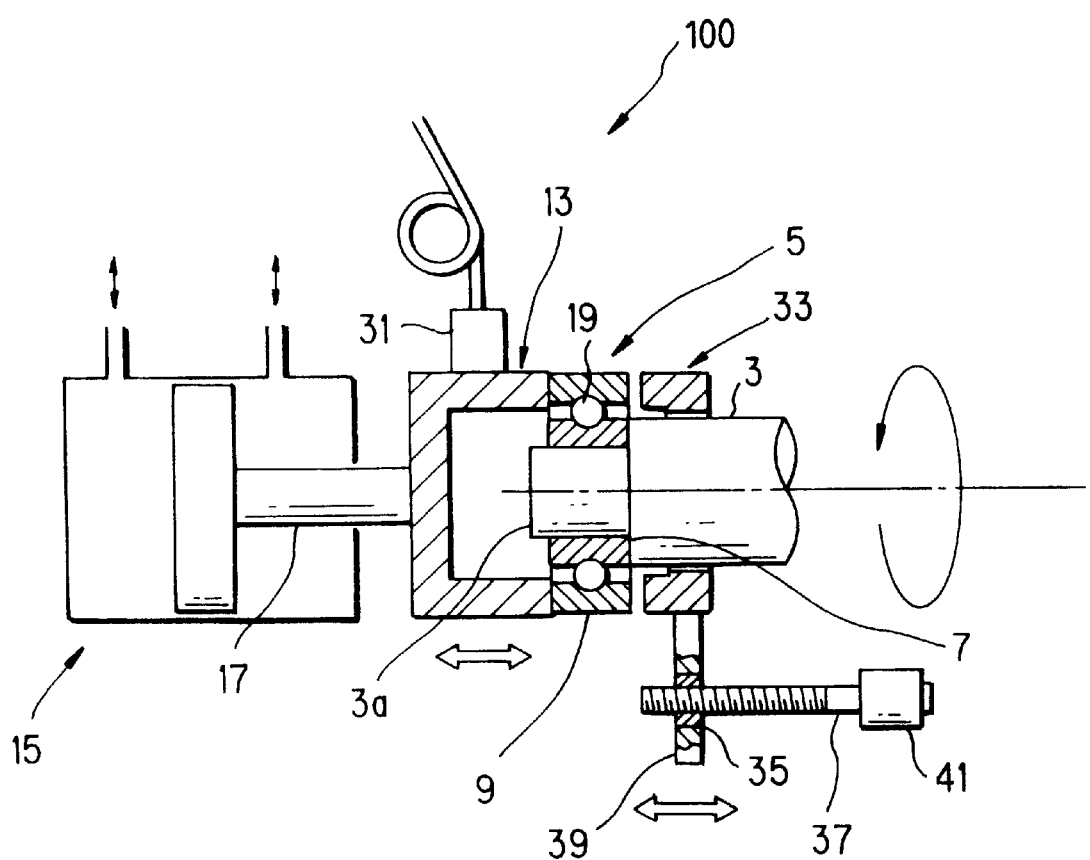
FIG. 1 is a configuration view of a ball bearing inspection apparatus according to the present invention.
Figure 2:
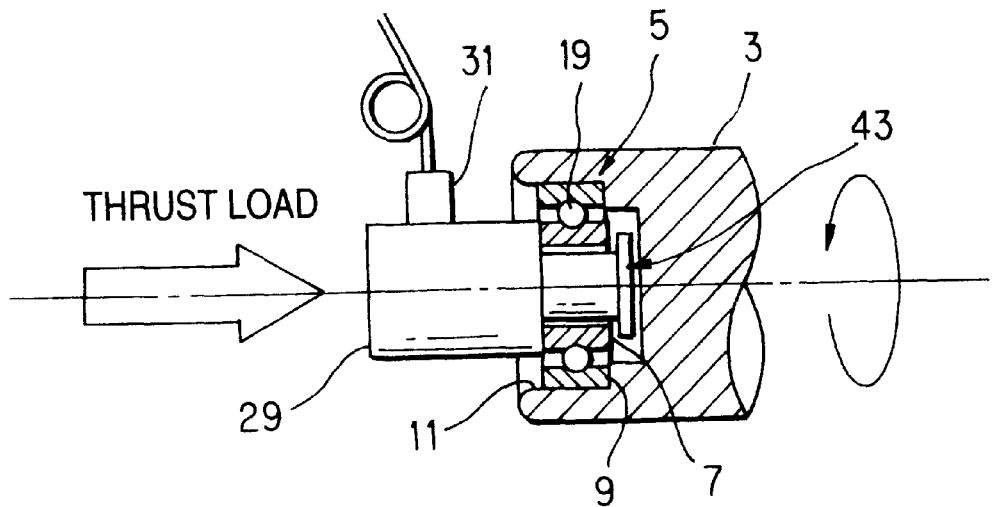
FIG. 2 is a configuration view showing a modified example of the ball bearing inspection apparatus depicted in FIG. 1 in the case where an outer race is rotated.
Figure 3:
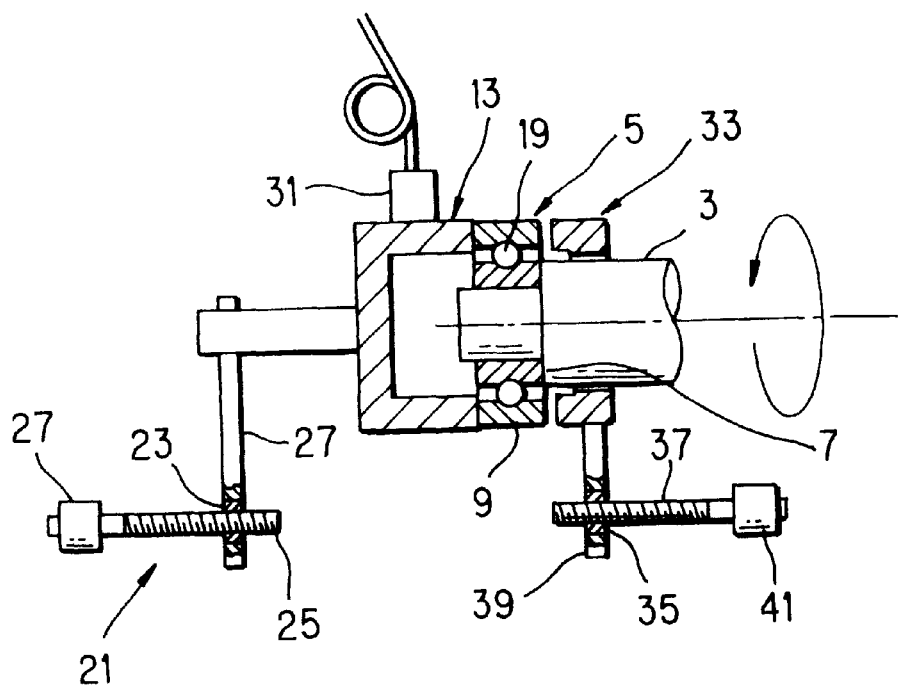
FIG. 3 is a configuration view showing a modified example of the ball bearing inspection apparatus having a pressing mechanism different from that in FIG. 1.

FIG. 1 is a view showing the configuration of a first embodiment of the ball bearing inspection apparatus according to the present invention, FIG. 2 is a configuration view showing a modified example of the ball bearing inspection apparatus depicted in FIG. 1 in the case where an outer race is rotated, and FIG. 3 is a configuration view showing a modified example of the ball bearing inspection apparatus having a pressing mechanism different from that in FIG. 1.

In a ball bearing inspection apparatus 100 in this embodiment, a rotation shaft 3 is provided so as to be rotated by means of a motor not shown. The axial movement of the rotation shaft 3 is limited. The rotation shaft 3 is removably attached to either of the inner circumference of an inner race 7 and the outer circumference of an outer race 9 in a ball bearing 5 so that one of the inner and outer races 7 and 9 is rotated. In this embodiment shown in FIG. 1, a small diameter portion 3a is formed at an end of the rotation shaft 3 so that the inner circumference of the inner race 7, which is one of the inner and outer races 7 and 9, is fitted to the outer circumference of the small diameter portion 3a.

Alternatively, the rotation shaft 3 may be designed so that the outer race 9, which is the other one of the inner and outer races 7 and 9, is fitted to the rotation shaft 3. In this case, a fitting recess 11 may be formed at an end of the rotation shaft 3 and fitted to the outer circumference of the outer race 9 so that the outer race 9 is rotated as shown in FIG. 2.

As shown in FIG. 1, a press plate 13 is disposed on an opposite side of the rotation shaft 3 with respect to the ball bearing 5 fitted to the rotation shaft 3. For example, the press plate 13 is shaped like a bottomed cylinder opened at an end so that the end abuts on a side face of the outer race 9. The press plate 13 is supported to be not rotatable. Hence, the outer race 9 in contact with the press plate 13 rotates relative to the inner race 7 because the rotation of the outer race 9 is limited.

A drive shaft 17 of a pressing-driving cylinder 15 is connected to a bottom portion of the press plate 13. Hence, the press plate 13 presses the outer race 9 in an axial direction of the rotation shaft 3 (to the right in FIG. 1) by expansion-driving the drive shaft 17 of the cylinder 15. That is, because the axial movement of the inner race 7 in the ball bearing 5 is limited by the rotation shaft 3, a thrust load to the right in FIG. 1 is applied to the outer race 9. Hence, in the ball bearing 5, the outer race 9 is displaced in the axial direction from the inner race 7 so that a pre-load is applied to balls 19.

Although the above description has been made upon the case where the ball bearing inspection apparatus 100 uses the cylinder 15 shown in FIG. 1 as a press-drive source for the press plate 13, the present invention may be applied also to the case where a ball screw mechanism 21 shown in FIG. 3 is used as the press-drive source. In this case, a press arm 24 thread-engaged with a ball screw 25 through a nut 23 is linked to a bottom portion of the press plate 13. Hence, when the ball screw 25 is rotated by means of a servo-motor 27, the press plate 13 presses the outer race 9 in the axial direction of the rotation shaft 3 (to the right in FIG. 1) so that a thrust load can be applied to the outer race 9 in the same manner as described above.

Further, in a modified example in which the outer race 9 is rotated as shown in FIG. 2, the inner race 7 is pressed in the axial direction of the rotation shaft 3 (to the right in FIG. 2) by a shaft-like press plate 29. Also in this case, a cylinder 15 or a ball screw mechanism 21 may be used as a press-drive source. Also in this modified example, a thrust load is applied to the inner race 7 by the press plate 29, so that the outer race 9 is displaced in the axial direction from the inner race 7 to thereby apply a pre-load to the balls 19 of the ball bearing 5.

A vibrometer 31 is attached to the press plate 13 (the shaft-like press plate 29 in the modified example). The vibrometer 31 is provided to detect vibration (sound) of the ball bearing 5 caused by rotation when the ball bearing 5 is rotated by the rotation shaft 3. The vibrometer 31 is electrically connected to a judgment control circuit not shown. The judgment control circuit is provided to judge on the basis of a detection signal received from the vibrometer 31 whether any one of surfaces of the balls 19 has a defect or not.

Further, an annular press-back plate 33 is disposed on the outer side of the rotation shaft 3 so as to be movable in the axial direction of the rotation shaft 3. A press arm 39 thread-engaged with a ball screw 37 through a nut 35 is linked to the press-back plate 33. The press-back plate 33 is provided to press the outer race 9 in the axial direction of the rotation shaft 3 (to the left in FIG. 1) when the ball screw 37 is rotated by means of a servo-motor 41. On this occasion, a thrust load to the left in FIG. 1 is applied to the outer race 9 of the ball bearing 5 because the inner race 7 of the ball bearing 5 is fitted to the rotation shaft 3 so that the axial movement of the inner race 7 is limited. Hence, the outer race 9 is displaced in a direction reverse to the pressing direction of the press plate 13, so that a pre-load in a direction reverse to the direction in the case of pressing due to the press plate 13 is applied to the balls 19 of the ball bearing 5. That is, the direction of pressing of the outer race 9 is changed over by the press plate 29 and the press-back plate 33 alternately.

Incidentally, in a modified example in which the outer race 9 is rotated as shown in FIG. 2, a press-back plate 43 is disposed in a fitting recess 11 of the rotation shaft 3. The press-back plate 43 is formed so that the inner race 7 is pressed in the axial direction of the rotation shaft 3 (to the left in FIG. 2) by a cylinder or a ball screw mechanism not shown. Also in the modified example, the inner race 7 of the ball bearing 5 is displaced in a direction reverse to the pressing direction of the press plate 29, so that a pre-load in a direction reverse to the direction in the case of pressing due to the press plate 29 is applied to the balls 19.

A method for inspecting a ball bearing by use of the ball bearing inspection apparatus 100 configured as described above will be described while the case where the inner race 7 is rotated as shown in FIG. 1 is taken as an example.

Figure 4:
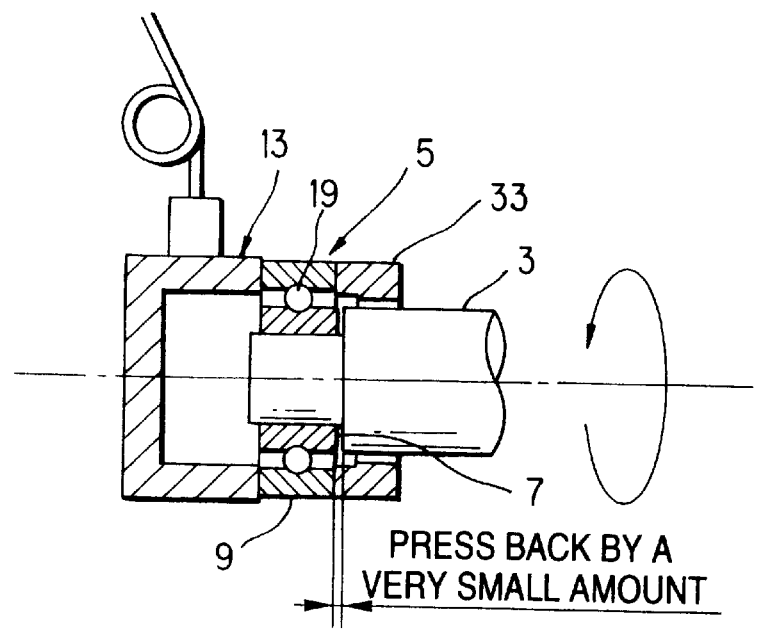
FIG. 4 is a configuration view of a main part showing a state in which an outer race of a ball bearing installed into the ball bearing inspection apparatus depicted in FIG. 1 is pressed back.
Figure 5A:
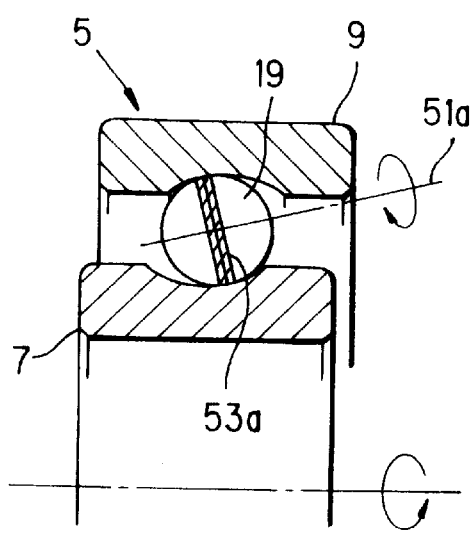
FIGS. 5A and 5B are explanatory views showing ball's own rotation axis which changes on the basis of changing-over of the pressing direction.
Figure 5B:
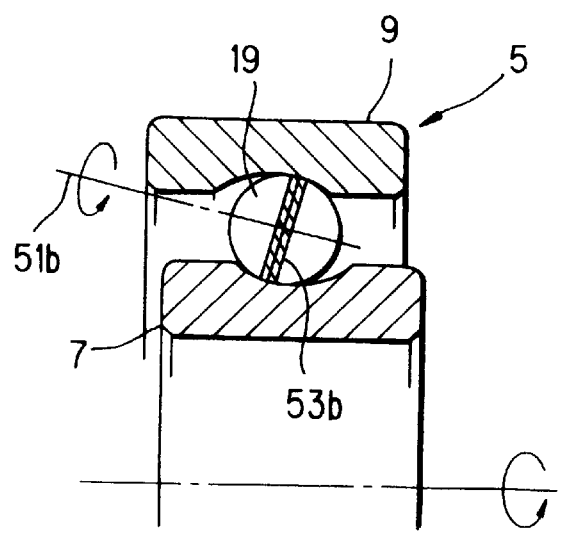
Figure 6:
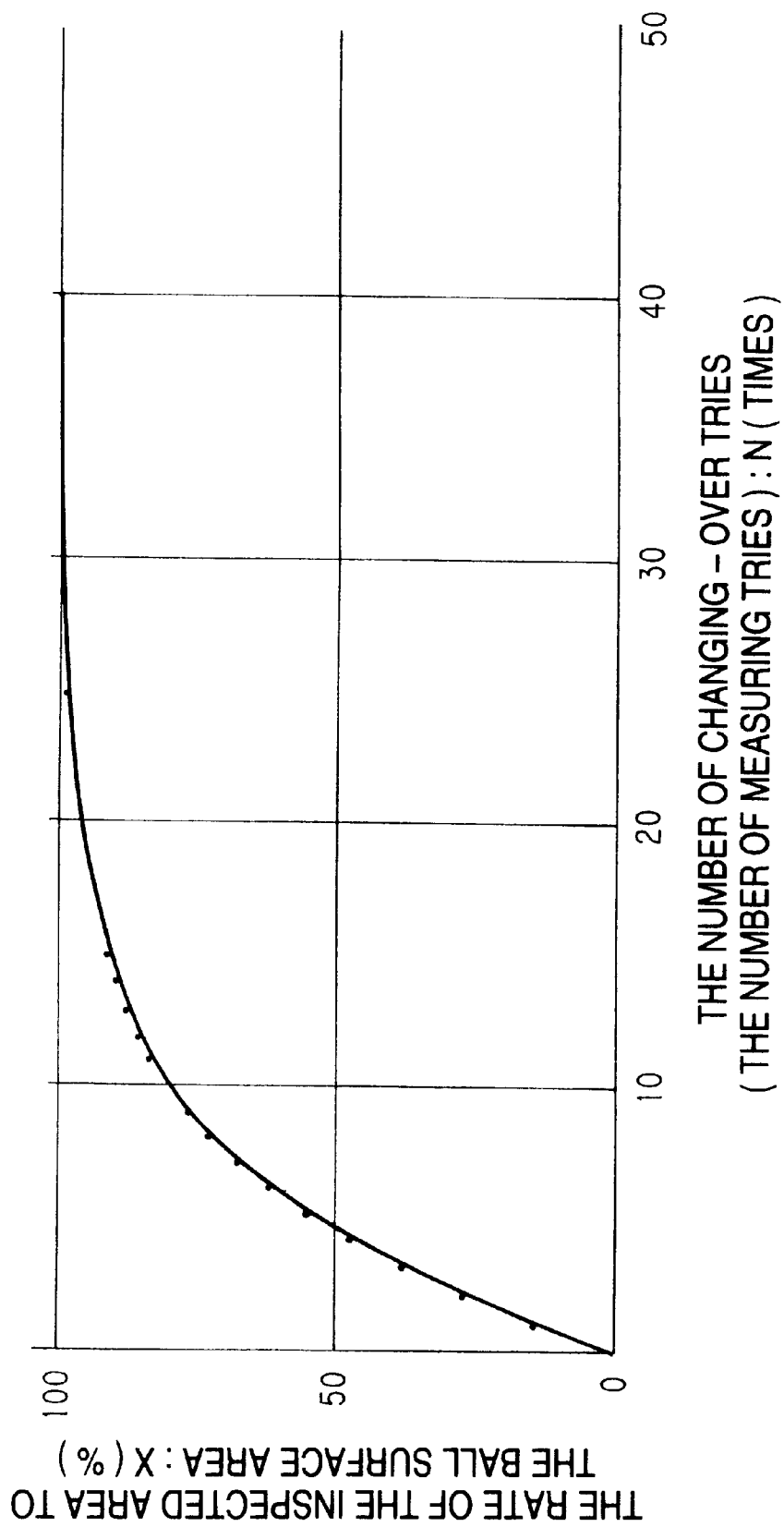
FIG. 6 is a graph showing the relation between the number of changing-over of the pressing direction and the inspected area.

FIG. 4 is a configuration view of a main part showing a state in which the outer race of the ball bearing installed into the ball bearing inspection apparatus is pressed back, FIGS. 5A and 5B are explanatory views showing a ball's own rotation axis which changes on the basis of changing-over of the pressing direction, and FIG. 6 is a graph showing the relation between the number of tries to change over the pressing direction (the number of measuring tries) and the rate(percentage) of inspected area.

To inspect the ball bearing 5 for defects by use of the ball bearing inspection apparatus 100, first as shown in FIG. 1, the inner race 7 of the ball bearing 5 is rotated by driving the rotation shaft 3 in the condition that the inner race 7 is attached to the rotation shaft 3 (rotating step). Then, the outer race 9 is pressed in the axial direction of the rotation shaft 3 by use of the press plate 13 disposed on an opposite side of the rotation shaft 3 (pressing step). As a result, a pre-load is applied to the balls 19, so that each of the balls 19 rolls around its own rotation axes 51a inclined up to the right as shown in FIG. 5A. On this occasion, a constant contact area (running trace) 53a of the surface of the ball 19 contacts race faces of the inner and outer races 7 and 9.

As shown in FIG. 4, the outer race 9 in this condition is pressed back by a very small distance in a direction reverse to the pressing direction of the press plate 13 by use of the press-back plate 33 so that the pressing direction given to the ball bearing 5 is changed over instantaneously (pressing-back step). The distance required for pressing back the outer race 9 varies in accordance with the size of the ball bearing 5 but is generally in a range of from 0.1 to 2 mm. As a result, each of the balls 19 in the ball bearing 5 rolls around its own rotation axis 51$b$ inclined up to the left as shown in FIG. 5B. (That is, an angle defined by the ball's own rotation axes and the rotation shaft in the pressing step and that in the pressing-back step are reversed.) On this occasion, a running trace 53$b$ of the ball 19 different from the running trace 53$a$ contacts race faces of the inner and outer races 7 and 9.

After the pressure (thrust load) due to the press-back plate 33 is removed in this condition, the outer race 9 is pressed to the right in the axial direction of the rotation shaft 3 again by use of the press plate 13 as shown in FIG. 1 (re-pressing step). As a result, each of the balls 19 rolls around a rotation axis different from the initial rotation axis 51$a$, so that the running trace also changes from the initial one 53$a$. (Note that even if the angle of the balls' own rotation axes in the pressing step is the same in degree as that in the pressing-back step, each of the balls 19 rolls around a rotation axis different from the initial rotation axis 51$a$.) This is because the angle of the ball's own rotation axis and the rotational speed of the ball change at random when the pressing direction is changed over in the process from the pressing step to the pressing-back step and the angle of the ball's own rotation axis and the rotational speed of the ball change at random when the pressing direction is further changed over in the process from the pressing-back step to the re-pressing step.

Hence, according to the aforementioned ball bearing inspection apparatus 100, the pressing direction can be changed over by a large number of times to apply thrust loads in opposite axial directions alternately to the ball bearing 5 at one installing try. Hence, the running trace of the balls at the time of measurement changes largely, so that a large part of the ball surfaces can be inspected in a short time.

For example, the number of changing-over (inspection) tries is calculatively given by the formula $$X=[1-\{1-(S/100)^N\}]\times 100$$

in which:
- $S$ [%] is the rate of the running area (inspected area) to the ball surface area at one changing-over (inspection) try;
- $N$ [times] is the number of changing-over (inspection) tries; and
- $X$ [%] is the rate of the running area (inspected area) to the ball surface area at N changing-over (inspection) tries.

In this formula, S is determined on the basis of the contact width of the bearing calculated by use of the Hertzian elastic contact theory (for example, see "Ball Bearing Lubrication", pp. 68–74, 1981, John Wiley & Sons., written by Hamrock & Dowson.).

Hence, difference occurs in accordance with the design size of the ball bearing and the inspecting condition. Assuming now S=15%, the relation between N and X is as shown in FIG. 6, that is, as follows.

X=80.3% for N=10
X=91.3% for N=15
X=96.1% for N=20
X=98.3% for N=25
X=99.2% for N=30
X=99.8% for N=40

Figure 7:
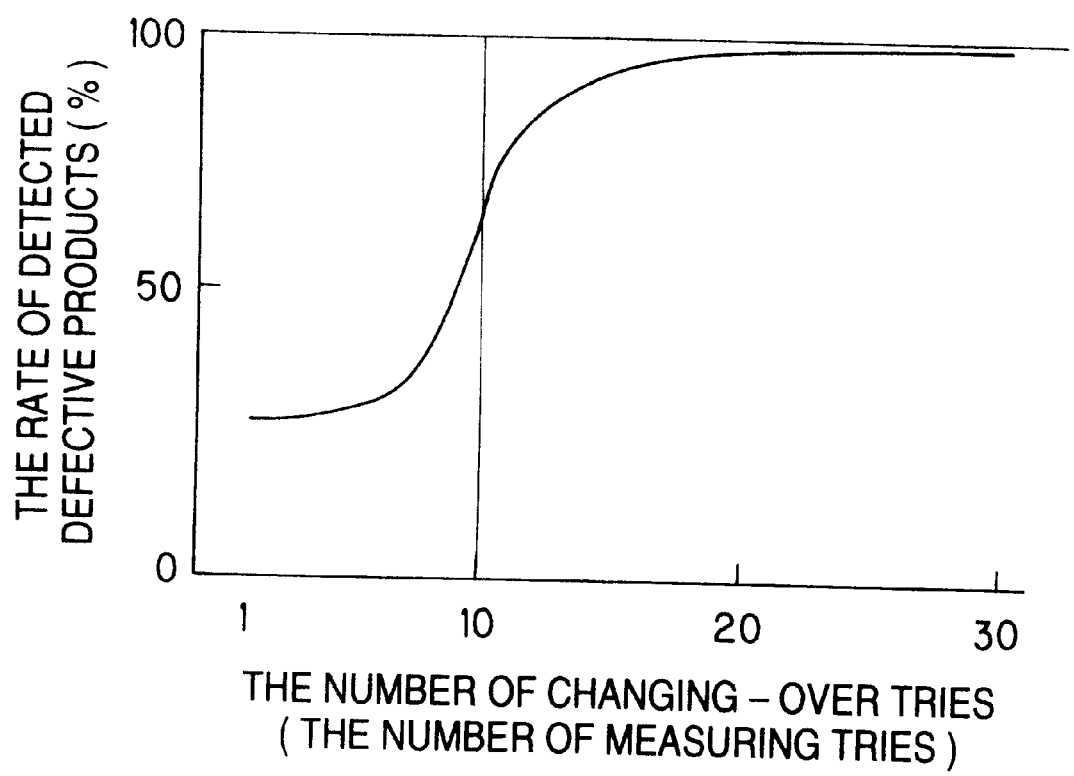
FIG. 7 is a graph showing a result of examination of the relation between the number of changing-over of the pressing direction and the rate(percentage) of detected defective products.

The relation between the number of changing-over tries and the rate of detected defective products was examined upon 100 ball bearings having defective balls in the construction of a bearing inner diameter of φ5 mm, a bearing outer diameter of φ13 mm, a width of 4 mm and a ball diameter of φ2 mm. FIG. 7 is a graph showing a result of the examination.

It is apparent from the result shown in FIG. 7 that the ability of detecting defects is improved greatly when the number N of changing-over (inspection) tries is set to be not smaller than 10, that is, when the rate X of the inspected area is set to be not lower than 80%. Moreover, defects can be detected so as to be little missed when the number N of changing-over (inspection) tries is set to be not smaller than 25, that is, when the rate X of the inspected area is set to be not lower than 98%.

That is, when the rate X of the inspected area is set to be not lower than 80%, the probability of detection of defects can be improved greatly compared with the conventional one. More preferably, when the rate X of the inspected area is set to be not lower than 98%, greater improvement in the detecting ability can be attained.

Incidentally, when the ball screw mechanism 21 as shown in FIG. 3 is used as a substitute for the cylinder 15, drive control for pre-load can be made easily because driving of each of the press plate 13 and the press-back plate 33 is controlled by a servo-motor. Hence, the drive mechanism can be simplified.

Figure 8:
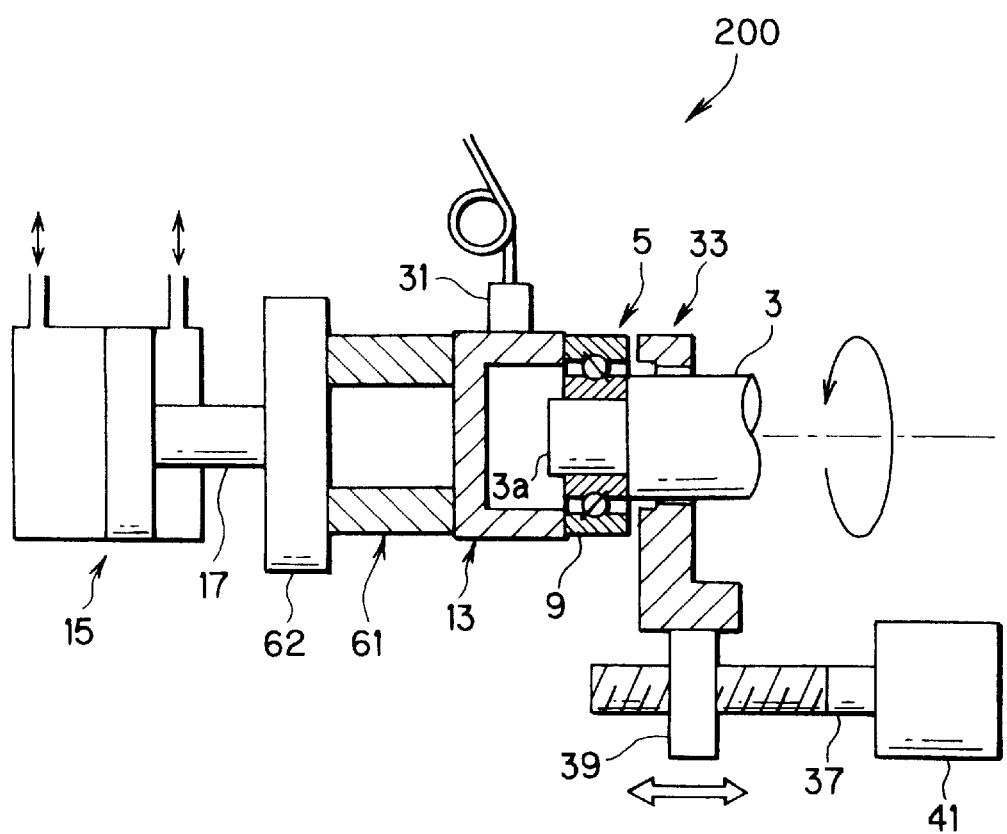
FIG. 8 is a view showing the configuration of a second embodiment of the ball bearing inspection apparatus according to the present invention.

A second embodiment of the ball bearing inspection apparatus according to the present invention will be described below. FIG. 8 is a configuration view of the ball bearing inspection apparatus in this embodiment. Parts having the same functions as those in the ball bearing inspection apparatus 100 shown in FIG. 1 are referred to by the same reference characters respectively and the description thereof will be omitted hereafter.

As shown in FIG. 8, in the ball bearing inspection apparatus 200 in this embodiment, a bottom portion of a press plate 13 attached to a vibrometer 31 is fixed to a pedestal 62 through a damper member 61 such as an O-ring, a rubber material, a plastic material, or the like, having a vibration damping function. Further, the pedestal 62 is fixed to a drive shaft 17 so as to be able to be interlocked with the drive shaft 17.

A drive force transmitted from the cylinder 15 to the drive shaft 17 is applied to the press plate 13 through the damper member 61, so that vibration applied to the press plate 13 at the time of press-driving is damped. As a result, the noise of vibration transmitted from the drive shaft 17 is blocked. Hence, accuracy in vibration measurement due to the vibrometer 31 can be improved, so that more accurate ball bearing inspection can be made.

Figure 9:
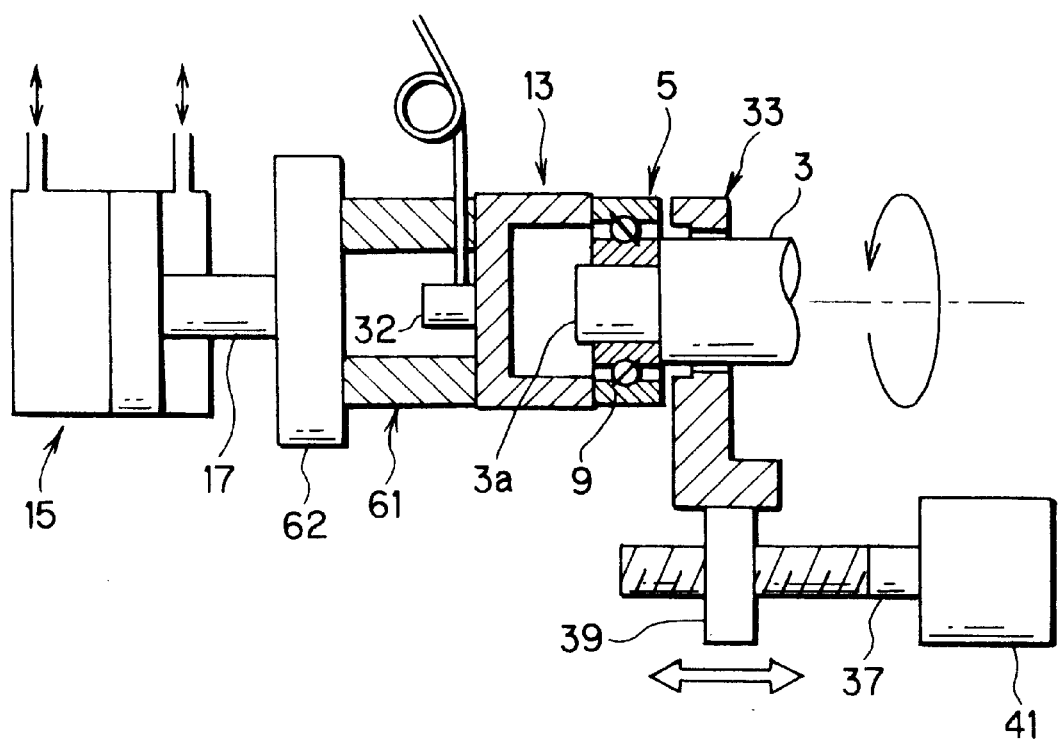
FIG. 9 is a view showing a modified example which is designed to measure vibration in an axial direction.

Although the above description has been made upon the case where the vibrometer 31 measures the radial vibration of the press plate 13, the present invention may be applied also to the case where the axial vibration of the press plate 13 is measured. FIG. 9 shows a modified example of this embodiment in which such axial vibration is measured. In this modified example, a vibrometer 32 is disposed on the bottom portion of the press plate 13 and in the position on the rotation axis of the rotation shaft so that the axial vibration applied to the press plate 13 can be measured.

Figure 10:
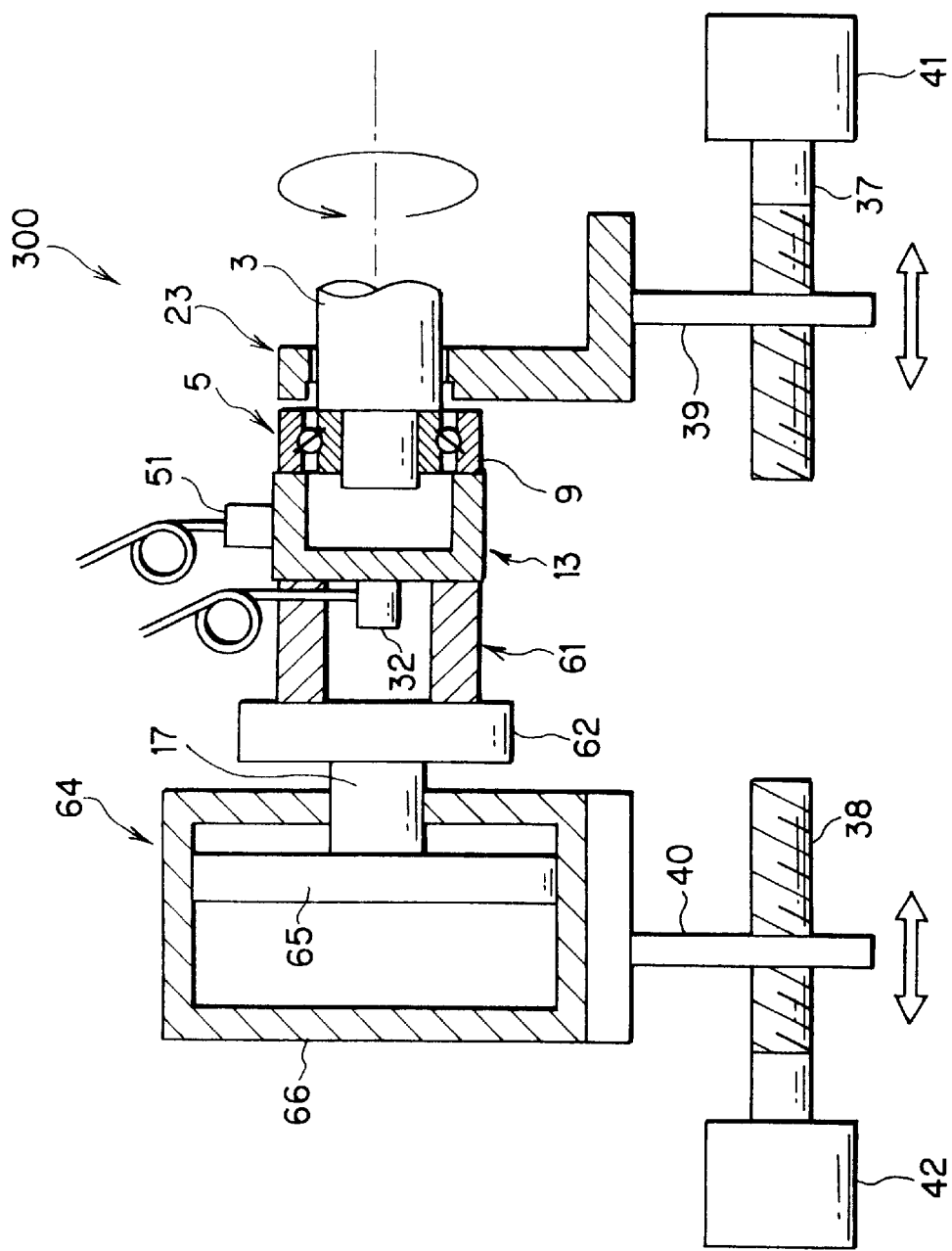
FIG. 10 is a view showing the configuration of a third embodiment of the ball bearing inspection apparatus according to the present invention.

A third embodiment of the ball bearing inspection apparatus according to the present invention will be described below. FIG. 10 is a configuration view of the ball bearing inspection apparatus in this embodiment. Similarly to the previous embodiment, parts having the same functions are referred to by the same reference characters and the description thereof will be omitted hereafter.

As shown in FIG. 10, in the ball bearing inspection apparatus 300 in this embodiment, a bottom portion of the press plate 13 attached both to the vibrometer 31 for measuring radial vibration and to the vibrometer 32 for measuring axial vibration is fixed to the pedestal 62 through the damper member 61. The pedestal 62 is connected to a piston 65 of an air cylinder 64 through the drive shaft 17 so that a pressing force from the air cylinder 64 is transmitted to the press plate 13 side.

Further, a box 66 of the air cylinder 64 is linked to a press arm 40 thread-engaged with a ball screw 38 through a nut. The ball screw 38 is rotated by means of a servo-motor 42 to thereby adjust the pressure applied to the piston 65.

In this configuration of the ball bearing inspection apparatus, the pressing force from the air cylinder 64 side to the press plate 13 side can be adjusted to a desired amount by driving of the servo-motor 42 so that the press plate 13 always applies a constant pressing force to the ball bearing 5. As a result, a constant pre-load is applied to the ball bearing 5.

When, in this condition, the press-back plate 33 is pressed to the ball bearing 5 side by driving of the servo-motor 41 or the pressure due to the press-back plate 33 is removed, the balls' own rotation axes of the balls in the ball bearing 5 can be changed as shown in FIGS. 5A and 5B.

In this manner, the operation of changing the direction of pressing the ball bearing over can be made easily by operating only the press-back plate 33 in the condition that a constant pre-load is applied to the ball bearing 5 by the air cylinder 64. As a result, the balls' own rotation axes can be changed easily by simple control, so that the ball bearing can be inspected more quickly.

Figure 11:
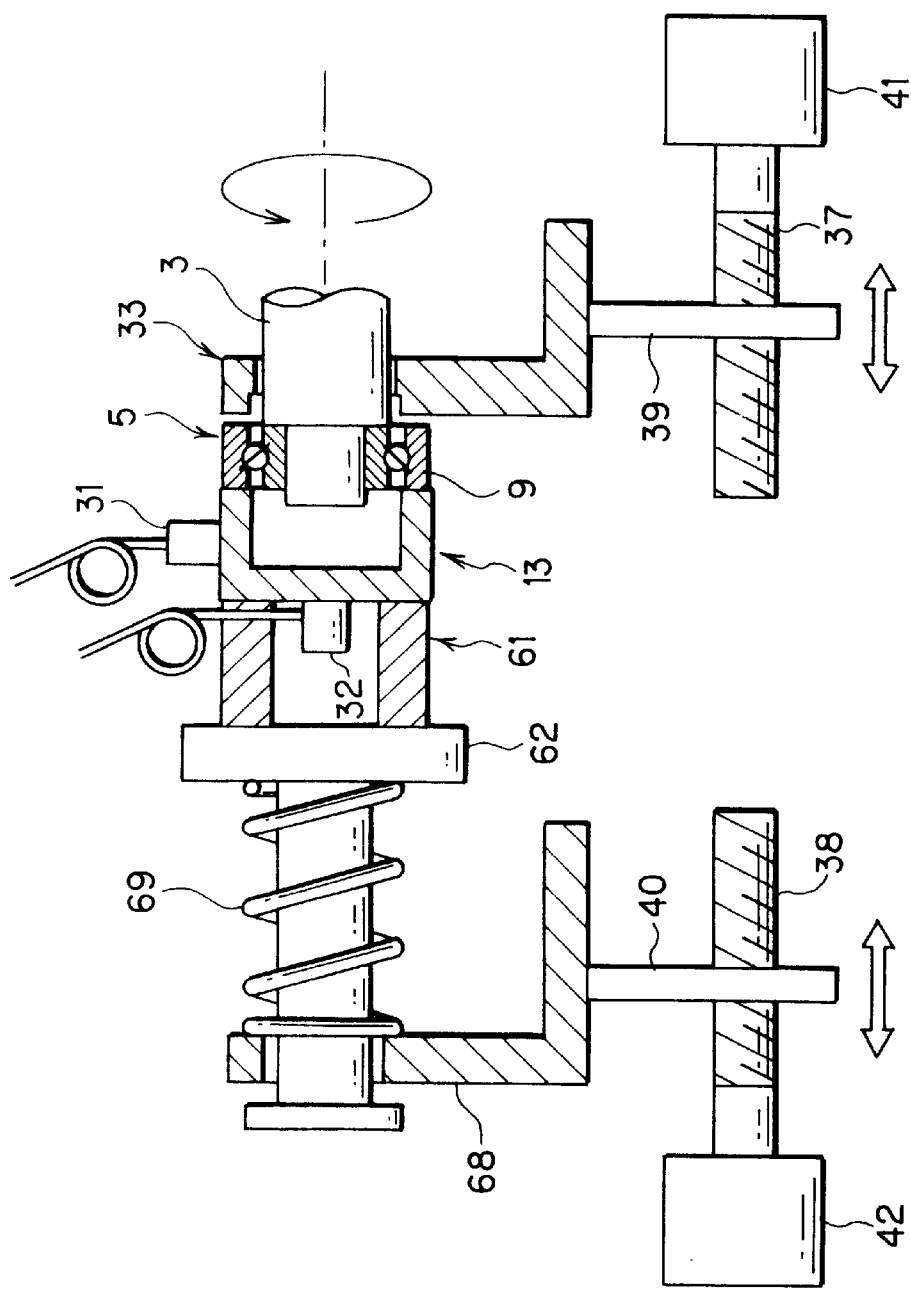
FIG. 11 is a view showing a modified example which is designed so that pre-loading is made by a coiled spring.

This embodiment may be modified so that a pre-load is given by an elastic body or an elastic material such as a spring, or the like, as a substitute for the air cylinder 64. FIG. 11 shows a modified example of this embodiment in which a pre-load is given by a coiled spring. In this embodiment, a coiled spring 69 is disposed between the pedestal 62 and a support member 68 so that the pedestal 62 is pressed toward the ball bearing 5 by the coiled spring 69. Further, the support member 68 is linked to the press arm 40. Hence, when the coiled spring 69 is contracted by drive of the servo-motor 42, the pre-load applied to the ball bearing 5 can be adjusted to be a desired amount.

Also in this configuration, the operation of changing the direction of pressing of the ball bearing 5 over can be made easily by operating only the press-back plate 33 in the condition that a constant pre-load is applied to the ball bearing 5.

In the ball bearing inspection apparatus according to the aforementioned embodiments, the following effects are obtained in addition to the effect that a large area of the ball surfaces can be inspected in a short time.

That is, defective bearings can be prevented from flowing out because the probability of detection of defective balls 19 is improved.

Feedback to the production step in which surface defects may occur in the balls can be made by analyzing the level, number, etc. of pulses generated from defective bearings.

Development to the conventional ball bearing inspection apparatus can be made by a simple means of changing the sequence program if the press-back mechanism is added to the apparatus.

In addition, the probability of detection of vibration caused by foreign matter contamination of the inside of a bearing can be also improved because lubricating oil in the inside of the bearing is stirred sufficiently.

While there has been described in connection with the preferred embodiment of the invention, it will be obvious to those skilled in the art that various changes and modifications may be made therein without departing from the invention, and it is aimed, therefore, to cover in the appended claim all such changes and modifications as fall within the true spirit and scope of the invention.

As described above in detail, the ball bearing inspection apparatus according to the present invention comprises a rotation shaft for rotating one of inner and outer races, a press plate for pressing the other of the inner and outer races, and a press-back plate for pressing back the other race in a direction reverse to the pressing direction of the press plate. Hence, the direction of pressure applied to the other race can be changed over reversely. By this, the contact surfaces of the balls change because the balls' own rotation axes change whenever the pressing direction is changed over. As a result, a large area of the ball surfaces can be inspected in a short time by changing the pressing direction over by a plurality of times at one installing try.

What is claimed is:

1. A ball bearing inspection method for inspecting a ball surface state of a ball bearing comprising:

rotating a first race of the ball bearing, which is fitted to a rotation shaft, by the rotation shaft while limiting the movement of the first race in an axial direction of the rotation shaft;

pressing a second race in an axial direction of the rotation shaft while limiting the rotation of the second race by use of a press plate disposed on an opposite side of the rotation shaft with respect to the ball bearing, to thereby apply a first thrust load to one of end surfaces of said second race in the axial direction with said press plate;

pressing back said second race in a direction reverse to the second race pressing direction of the press plate by use of a press-back plate which is provided movably in the axial direction of the rotation shaft, to thereby apply a second thrust load to the other end surfaces of said second race in the axial direction with said press-back plate; and measuring vibration generated in a vibrometer attached to said press plate while relatively rotating said first and second races and also alternatively applying said first and second thrust loads to said second race, wherein said first race is one of an inner race and an outer race, and said second race is the other of said inner race and said outer race, wherein when said first and second thrust loads are alternatively applied to said second race, an inclination of a rotation axis of the ball relative to the rotational axis of the bearing are changed over.

2. The ball bearing inspection method according to claim 1, wherein an inclination of the rotation axis of the ball when said second race is pressed by said press plate and an inclination of the rotation axis of the ball when said second race is pressed back by said press-back plate are substantially opposite to each other with respect to the rotation shaft.

3. The ball bearing inspection method according to claim 1, wherein said vibration is measured when said first thrust load is applied to said second race.

4. A ball bearing inspection method for inspecting a ball surface state of a ball bearing comprising:

rotating a first race of the ball bearing, which is fitted to a rotation shaft, by the rotation shaft while limiting the movement of the first race in an axial direction of the rotation shaft;

pressing a second race in an axial direction of the rotation shaft while limiting the rotation of the second race by use of a press plate disposed on an opposite side of the rotation shaft with respect to the ball bearing, to thereby apply a first thrust load to one of end surfaces of said second race in the axial direction with said press plate;

pressing back said second race in a direction reverse to the second race pressing direction of the press plate by use of a press-back plate which is provided movably in the axial direction of the rotation shaft, to thereby applying a second thrust load to the other end surfaces of said second race in the axial direction with said press-back plate; and measuring vibration generated in a vibrometer attached to said press plate while relatively rotating said first and second races and also alternatively applying said first and second thrust loads to said second race, wherein said first race is one of an inner race and an outer race, and said second race is the other of said inner race and said outer race, and wherein the pressing step and the pressing back step are repeated successively by a predetermined number of times which is larger than a number to make a rate of an inspected area to a ball surface area to be not lower than 80% when a running area is calculated on the basis of a following calculation formula:

$$x=[1-\{1-(S/100)^N\}]\times 100$$

where:
N [times] is said predetermined number of repetition;
S [%] is a rate of the running area to the ball surface area at one repetition; and
X [%] is a rate of the running area to the ball surface area at said predetermined number of repetition.

5. The ball bearing inspection method according to claim 4, wherein said predetermined number of repetition is larger than a number of repetition where said rate of the running area to the ball surface area at said predetermined number of repetition is not lower than 98%.

6. A ball bearing inspection apparatus for inspecting a ball surface state of a ball bearing, said apparatus comprising:
a rotation shaft fittable to a first race for rotating said first race while limiting an movement of said first race in an axial direction of said rotation shaft;
a press plate disposed on an opposite side of said rotation shaft with respect to said ball bearing for pressing a second race in said axial direction of said rotation shaft while limiting the rotation of said second race, to thereby apply a first thrust load to one of end surfaces of said second race with said press plate; and
a press-back plate provided so as to be movable in said axial direction of said rotation shaft for pressing back said second race in a direction reverse to the second race pressing direction of said press plate, to thereby apply a second thrust load to the other end surfaces of said second race with said press-back plate,
a measuring member for measuring vibration generated in a vibrometer attached to said press plate while relatively rotating said first and second races and also alternatively applying said first and second thrust loads to said second race,
wherein said first race is one of an inner race and an outer race, and said second race is the other of said inner race and said outer race,
wherein when said first and second thrust loads are alternatively applied to said second race, an inclination of a rotation axis of the ball relative to the rotational axis of the bearing are changed over.

7. The ball bearing inspection apparatus according to claim 6, further comprising:
a servo motor for driving at least one of said press plate and said press-back plate.

8. The ball bearing inspection apparatus according to claim 7, further comprising:
a damper disposed between a drive shaft of said servo motor and said at least one of said press plate and said press-back plate.

9. The ball bearing inspection apparatus according to claim 6, wherein said vibration is measured when said first thrust load is applied to said second race.

10. A ball bearing inspection method for inspecting a ball surface state of a ball bearing comprising:
rotating a rotatable race of the ball bearing, which is fitted to a rotation member, by the rotation member, while limiting the movement of the rotatable race in an axial direction of the rotation member;
pressing a stationary race in an axial direction of the rotation member while limiting the rotation of the stationary race by use of a press plate disposed on an opposite side of the rotation member with respect to the ball bearing, to thereby apply a first thrust load to one of end surfaces of said stationary race on the axial direction with said press plate;
pressing back said stationary race in a direction reverse to the stationary race pressing direction of the press plate by use of a press-back plate which is provided movably in the axial direction of the rotation member, to thereby apply a second thrust load to the other end surfaces of said stationary race in the axial direction with said press-back plate; and
measuring vibration generated in a vibrometer attached to said press plate while relatively rotating said rotatable and stationary races and also alternatively applying said first and second thrust loads to said stationary race,
wherein said rotatable race is one of an inner race and an outer race, and said stationary race is the other of said inner race and said outer race.

11. A ball bearing inspection method according to claim 10, wherein when said first and second thrust loads are alternatively applied to said stationary race, an inclination of the rotation axis of the ball relative to the rotational axis of the bearing is changed over from a positive value to a negative value.

12. The ball bearing inspection method according to claim 10, wherein an inclination of the rotation axis if the ball when said stationary race is pressed by said press plate and an inclination of the rotation axis of the ball when said stationary race is pressed back by said press-back plate are substantially opposite to each other with respect to the rotation member.

13. A ball bearing inspection apparatus for inspecting a ball surface state of a ball bearing, said apparatus comprising:
a rotation member fittable to a rotatable race for rotating said rotatable race while limiting a movement of said rotatable race in an axial direction of said rotation member;
a press plate disposed on an opposite side of said rotation member with respect to said ball bearing for pressing a stationary race in said axial direction of said rotation member while limiting the rotation of said stationary race, to thereby apply a first thrust load to one of end surfaces of said stationary race with said press plate; and a press-back plate provided so as to be movable in said stationary race in a direction reverse to the stationary race pressing direction of said press plate, to thereby apply a second thrust load to the other end surfaces of said stationary race with said press-back plate, a measuring member for measuring vibration generated in a vibrometer attached to said press plate while relatively rotating said rotatable and stationary races and also alternatively applying said first and second thrust loads to said stationary race, wherein said rotatable race is one of an inner race and an outer race, and said stationary race is the other of said inner race and said outer race.

14. The ball bearing inspection apparatus according to claim 13, wherein when said first and second thrust loads are alternatively applied to said stationary race, an inclination of the rotation axis of the ball relative to the rotational axis of the bearing is changed over from a positive value to a negative value.

15. The ball bearing inspection apparatus according to claim 13, further comprising:

a servo motor for driving at least one of said press plate and said press-back plate.

16. The ball bearing inspection apparatus according to claim 15, further comprising:

a damper disposed between a drive shaft of said servo motor and said at least one of said press plate and said press-back plate.

17. The ball bearing inspection apparatus according to claim 13, wherein said vibration is measured when said first thrust load is applied to said stationary race.

* * * * *